(12) United States Patent
Alman

(10) Patent No.: US 6,891,617 B2
(45) Date of Patent: May 10, 2005

(54) ASPECULAR MULTI-ANGLE PROTRACTOR FOR EVALUATING A SURFACE CONTAINING METALLIC PARTICLES

(75) Inventor: David H. Alman, Royal Oak, MI (US)

(73) Assignee: E.I. du Pont de Nemours and Company, Wilmington, DE (US)

(*) Notice: Subject to any disclaimer, the term of this patent is extended or adjusted under 35 U.S.C. 154(b) by 47 days.

(21) Appl. No.: 10/246,216

(22) Filed: Sep. 18, 2002

(65) Prior Publication Data
US 2004/0051873 A1 Mar. 18, 2004

(51) Int. Cl.[7] .................................................. G01J 3/46
(52) U.S. Cl. ........................................ 356/402; 356/244
(58) Field of Search ................................ 356/402, 405, 356/406, 407, 244

(56) References Cited

U.S. PATENT DOCUMENTS

| | | | |
|---|---|---|---|
| 3,349,665 A | | 10/1967 | Grosheim et al. |
| 3,708,233 A | * | 1/1973 | Van Dyk et al. ............. 356/244 |
| 3,712,745 A | * | 1/1973 | Armstrong, Jr. et al. .... 356/244 |
| 3,916,168 A | * | 10/1975 | McCarty et al. ............ 356/405 |
| 4,479,718 A | | 10/1984 | Alman |
| 4,917,495 A | | 4/1990 | Steenhoek |
| 5,231,472 A | | 7/1993 | Marcus et al. |
| 5,387,977 A | | 2/1995 | Berg et al. |
| 5,963,334 A | | 10/1999 | Yamaguchi et al. |
| 2002/0163640 A1 | | 11/2002 | Masuda |

FOREIGN PATENT DOCUMENTS

| | | |
|---|---|---|
| DE | 4109521 A1 | 10/1991 |
| DE | 199 50 588 A1 | 4/2001 |
| EP | 0 932 038 A1 | 7/1999 |
| JP | 59 159013 A | 1/1985 |
| JP | 63 048439 A | 7/1988 |
| JP | 1998010045 A | 1/1998 |
| JP | 1998281874 A | 10/1998 |
| JP | 2000 035375 A | 9/2000 |

OTHER PUBLICATIONS

International Search Report (PCT/US 03/29408) Dated Apr. 2, 2004.

* cited by examiner

Primary Examiner—F. L. Evans
(74) Attorney, Agent, or Firm—Steven C. Benjamin

(57) ABSTRACT

An apparatus, and method of use thereof, for multiangular visual evaluations of color properties of paint color samples which contain metallic flakes, comprising a cylindrical or semi-cylindrical shaped body capable of securing a color sample panel upon the central axis, wherein the circumference of the body has a partially glossy or mirrored reflective surface, and also has one or more marks indicating specific aspecular viewing angles relative to the plane of a color sample panel, thus allowing for improved correlation between visual and instrumental color evaluations of coated surfaces which contain metallic flakes.

9 Claims, 4 Drawing Sheets

ASPECULAR MULTI-ANGLE PROTRACTOR FOR EVALUATING A SURFACE CONTAINING METALLIC PARTICLES

BACKGROUND OF THE INVENTION

The invention is generally directed to an apparatus useful in evaluating optical properties of a surface containing metallic particles such as a paint containing metallic flakes. In particular, this invention is directed to an apparatus useful for visually evaluating color properties of a metallic paint, consistent with instrumental measurements.

The paint industry often utilizes light-reflecting flaked pigments in paints (i.e., metallic paints) to obtain pleasing aesthetic effects. Paints containing light-reflecting flaked pigment of such materials as aluminum, bronze, coated mica and the like are characterized by a "two-tone" or "flip-flop" effect whereby the apparent color of the paint changes at different viewing angles. This effect is due to the orientation of the flakes in the paint film. Since the color of such metallic paints will apparently vary as a function of the angle of illumination and viewing, multiple angled visual and/or spectrophotometric readings are required to accurately characterize the paint. See, for example, U.S. Pat. No. 4,479,718 issued Oct. 30, 1984 to Alman, the disclosure of which is herein incorporated by reference.

In the manufacture of pigmented paint, it is commonplace that simultaneous visual and instrumental color measurements are used in shading or batch release decisions. Most often, this situation exists due to geographic separation of the decision-makers along with a lack of instrumental equipment for all parties. As a result, a disparity between visual and instrumental color assessment for metallic and pearl colors frequently occurs, because simultaneous assessments are made at different aspecular angles. These disparities lead to inconsistencies between a color process operator's (shader's) assessment of color, and the measurement of a process system, such as a multi-angle spectrophotometer. These disparities quite often increase paint manufacturing time and become costly barriers to product batch release decisions between manufacturers and their respective customers.

A typical solution to compensate for the above described problem is installation and utilization of visual viewing equipment with fixed positions of the observer, light sources and multiple fixed positions of the paint color sample panel. An example is the Gretag MacBeth Skylight (C S McCamy) which has three light sources, fixed viewing port and five sample positions to provide 15 aspecular viewing angles between 10 and 110 degrees. However, this type of observation equipment is generally large, expensive, not considered mobile, and therefore has not been widely used in the industry.

Therefore, there is still a need for a color evaluation apparatus, which is mobile, inexpensive, and provides multiple fixed positions of viewing relative to the paint color sample panel.

SUMMARY OF THE INVENTION

There is provided by the present invention, a novel apparatus, and method of use thereof, for visual evaluation, at desired observation angles, of color properties of paint color samples which contain light-reflecting (e.g., metallic) flakes. The apparatus comprising a cylindrical or semi-cylindrical shaped body with two opposing slots to accept a color sample panel, and secure the panel upon the central axis of the body. The circumference of the body has a partially glossy or mirrored reflective surface, and also has one or more marks indicating specific aspecular viewing angles relative to the plane of the color sample panel. The aspecular viewing angles are those between the observation direction and the direction of specular reflection of a light source from the color sample surface. The reflective surface allows for identification and positioning of the light source, at the desired viewing angles. The overall benefit is improved correlation between visual and instrumental color evaluations of coated surfaces, which contain metallic flakes.

BRIEF DESCRIPTION OF DRAWINGS

The objects and features of the invention noted above are explained in more detail with reference to the drawings, in which like reference numerals denote like elements, and in which.

DETAILED DESCRIPTION OF THE INVENTION

In optically characterizing surfaces containing metallic particles such as metallic paints and films, it was recognized that directional reflectance had to be considered. Metallic paints contain light-reflecting flakes or platelets of such material as aluminum, bronze, coated mica and the like. These flakes or platelets function much like little mirrors, reflecting light directionally rather than in a diffuse manner. The directional reflectance characteristic of a metallic paint film results in a phenomenon known as goniochromatism, which is defined as the variation in color of a paint film as a function of the directions of illumination and viewing. This phenomenon is also sometimes described as "two-tone", "flop", "flip-flop", "flash", "side-tone", etc. In sum, the color of a metallic paint will appear different at different viewing angles.

In the manufacture of metallic particle containing paints, simultaneous visual and instrumental multi-angle color evaluations are commonly used in shading or batch release decisions. Shading is the process of adjusting the amounts of ingredients in a batch of paint so that the color of a sample made from the batch matches the color of a standard. A resulting disparity between visual and instrumental color evaluations for metallic paints frequently occurs, because they are made at different aspecular angles, at different sites. This situation commonly becomes a costly barrier to product batch release decisions between manufacturers and their respective customers. Thus, the object of the invention is to provide a visual color evaluation apparatus which is mobile, inexpensive, quick to use, and provides multiple fixed angular positions, correlatable to instrumental techniques.

Figure 1:
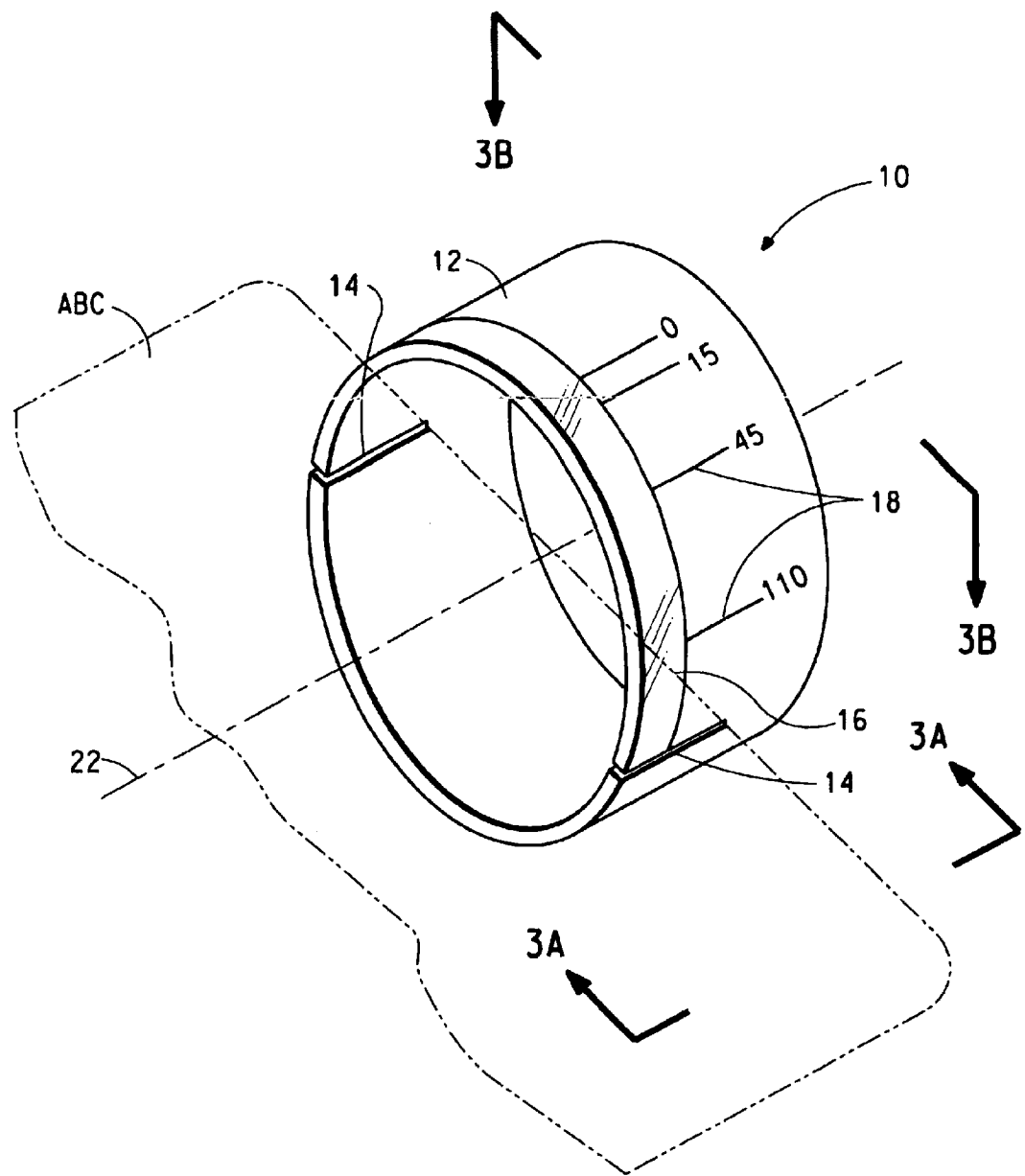
FIG. 1 is a perspective view of aspecular multi-angle protractor with a color sample panel in phantom view.

Referring to FIG. 1, a first embodiment of an aspecular multi-angle protractor apparatus according to the present invention, is generally designated by reference numeral 10. The apparatus 10 is comprised of a cylindrical or semi-cylindrical body 12, which includes a plurality of opposing slots 14 for accepting and securing a color sample panel ABC, upon the central axis of the body 12. The circumference of the body 12 has a partially mirrored surface 16 for identifying and assisting in the positioning of the body in relation to a light source. The circumference also includes marks 18, which indicate the aspecular viewing angle of the observer and light source, relative to the color sample panel ABC.

In regards to body 12 of the present invention, while various forms are possible, a cylindrical or semi-cylindrical shape is generally preferred. Alternatively, a conical, spherical, or even elliptical shapes may be used. The body may be a solid or hollow object, and may be manufactured of any material, including plastic or metal. In a preferred embodiment, the body 12 is a hollow cylindrical body manufactured of polyvinyl chloride material.

Figure 2:
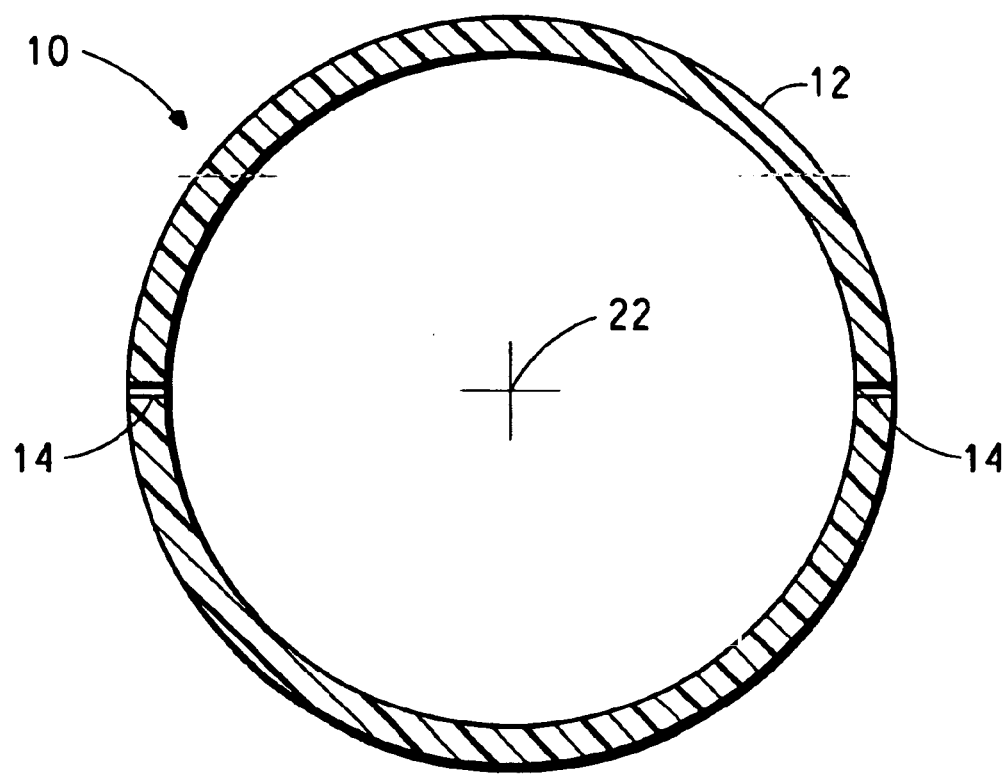
FIG. 2 is a cross-sectional view perpendicular to central axis 22 of FIG. 1.

As shown in FIG. 1, the body 12 has the ability to accept and secure a metallic paint containing color sample panel ABC upon the central axis 22 of the body. In a preferred embodiment, securing a color sample panel is accomplished with a plurality of slots 14, located on opposing sides, relative to central axis 22, of a hollow cylindrical body 12, as indicated in FIG. 2. Optionally, any method of positioning and securing a sample panel may be used, such as a clamp, flat ledge, or other. The method of accepting and securing may be designed to accommodate a variety of color panel sample substrates typically used in the field, such as steel, aluminum, or plastic.

Figure 3B:
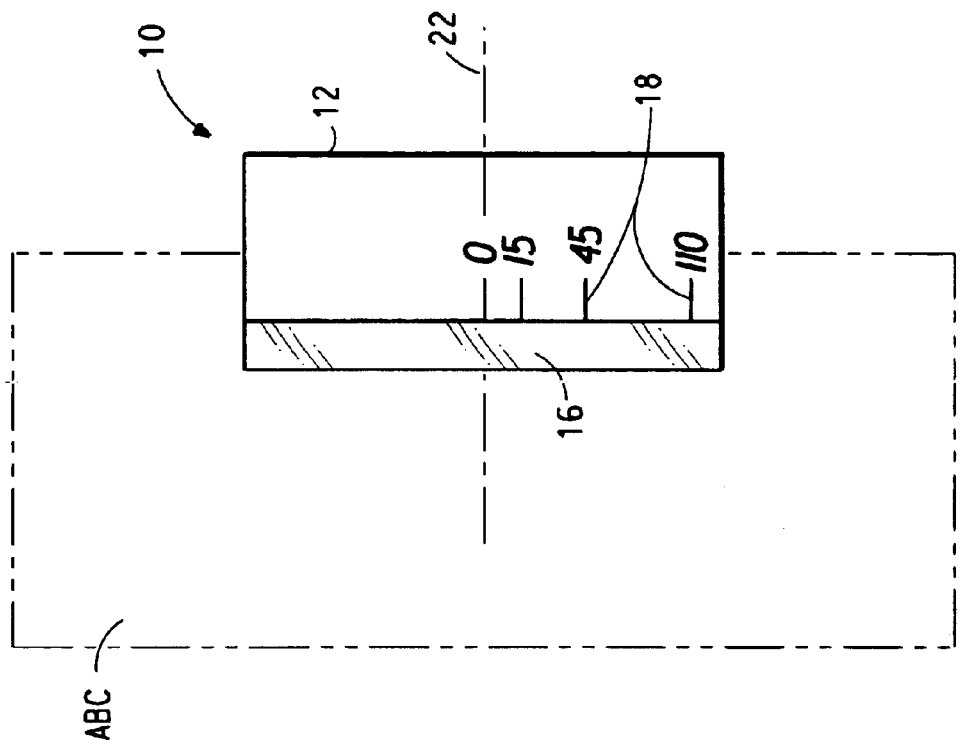
FIGS. 3A and 3B are 90 degree rotational views of the apparatus, orientated parallel to central axis 22 of FIGS. 1 and 2.
Figure 3A:
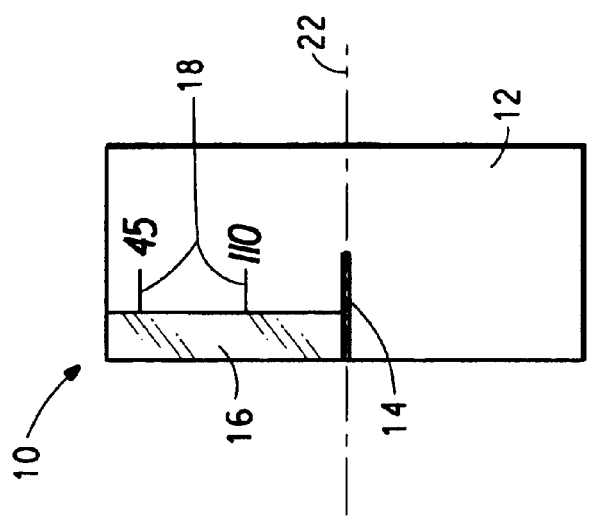

Body 12 is partially covered with a light reflective or mirrored surface 16, as shown in FIG. 1 and FIG. 3. The utility of this surface 16 is identification of a light source and positioning of the apparatus 10 in such a way allowing the viewer to evaluate the color sample panel ABC at a select angle between the light source and observer, relative to the sample panel. This reflective or mirrored surface is glossy and mirror-like in characteristic, and may be very bright, gray, or even black in color. In a preferred embodiment, two reflective surfaces, are utilized and orientated parallel to each other, the first being a glossy black surface, and the second, a silver-mirrored surface. These reflective surfaces are positioned upon the outer peripheral edge of the body. The glossy black surface is recommended for very bright light sources (i.e. the sun), while the silver-mirrored surface is more appropriate for dim or diffuse light sources.

As indicated in FIG. 1 and FIG. 3, the outer surface of body 12 is marked with numbers 18, at designated points about the circumference, the purpose of which is positioning the apparatus at a selected aspecular angle relative to a color sample panel ABC. The aspecular angle is that between the observation direction and the specular (or gloss) reflection direction. In a preferred embodiment, the apparatus 10 has alignment angles for gloss (0) and the three metallic color control angles (15°, 45°, 110°). These metallic color control angles are named near specular (15°), flat (45°) and high (110°) in DuPont Color Systems software. Alternatively, any aspecular angle, or combination thereof, could be utilized, as desired by the observer.

Figure 4:
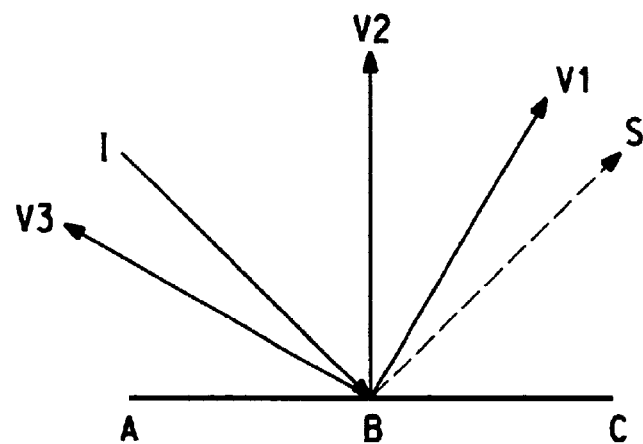
FIG. 4 illustrates the directions of illumination and viewing for an instrument to measure the color of flake-containing coatings at multiple viewing directions.

FIG. 4 illustrates the directions of illumination and viewing for an evaluation of the color of flake-containing coatings at multiple viewing directions (reference U.S. Pat. No. 4,479,718, previously incorporated). A color sample panel ABC is illuminated by a light source from direction I and is viewed in directions V1, V2, V3. The mirror reflection or specular reflection direction is indicated by the direction S. Defining the illumination and viewing directions as angles relative to a reference direction specifies the directional geometry of the measurement.

A particularly convenient reference direction for the angle specification is the specular direction, S. An aspecular angle of viewing is defined as the direction of viewing relative to the specular direction. Color measurement values such as tristimulus values (CIE X, Y, Z) or uniform color space values (CIE L*, a*, b*) for flake-containing coatings typically vary monotonically with increasing aspecular angle. Monotonic variation of color values would not be observed if other reference directions such as the color sample panel ABC, illumination direction I or surface normal V2 were chosen as the reference direction.

| Direction | Aspecular angle |
|---|---|
| I | 90 |
| V1 | 15 |
| V2 | 45 |
| V3 | 110 |

Figure 5:
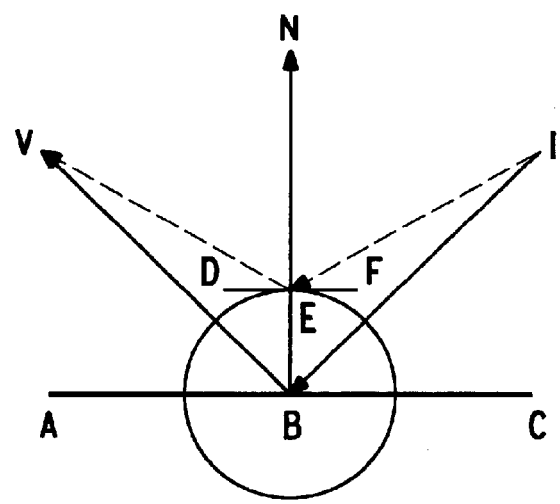
FIG. 5 is an end view of the aspecular protractor positioned to view a specular reflection direction.

FIG. 5 is an end view of the aspecular protractor positioned to view a specular reflection direction. In a preferred embodiment, color sample panel ABC slides into a pair of slots in the hollow cylindrical body with central axis at B. A light source at position I produces a glossy reflection at viewing position V since angle IBN equals angle VBN. A reference mark is placed on the circumference of the cylindrical body at a position E that is perpendicular to the plane ABC through the central axis B. Angles EBC and EBA are 90°.

An imaginary tangent DEF at position E is parallel to the color sample panel ABC. This tangent also gives a specular reflection of the light source I at the viewing direction V since angle IEN equals angle VEN. A mirrored or reflective surface 16 on the circumference of the body 12 will show a bright reflection of the light source at position E when the color sample panel is viewed at a specular reflection direction. The alignment point E is marked as the zero aspecular direction.

Figure 6:
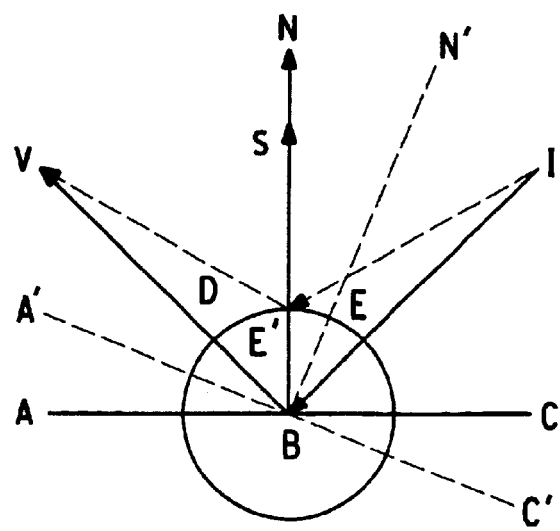
FIG. 6 is an end view of the aspecular protractor positioned to view an aspecular reflection direction.

FIG. 6 is an end view of the aspecular protractor positioned to view an aspecular reflection direction. If the body 12 is rotated through an angle of 22.5° so that coatings sample ABC is now at position A'BC' with surface normal at N', the specular direction is at S since angle IBN' equals angle SBN'. The viewing direction V is now at a direction 45° from the specular angle for the coating at A'BC'. The aspecular angle is twice the angle of rotation of the cylindrical body.

A mirror reflective surface on the cylindrical body will show a bright reflection of the light source at position E' when the coating is viewed at a 45° aspecular direction since the tangent at E' has equal angles IE'N and VE'N. An alignment mark 18 is made at E'. Other alignment marks 18 are provided on the circumference of the body 12 for desired aspecular viewing directions. For example:

| Aspecular viewing angle | Angles of alignment marks on the body circumference from position E |
| --- | --- |
| 0 | 0 |
| 15 | 7.5 |
| 45 | 22.5 |
| 110 | 55 |

When the reflected image of the light source is at one of the alignment marks the panels are viewed at the corresponding observation aspecular angle. This will help the observer to find agreement between visual observations and instrumental color measurements at the corresponding aspecular angles so that the color "looks like it reads."

In summary, this invention provides a novel, inexpensive, and mobile means to visually evaluate color properties of a color sample panel, consistent with instrumental measurements, by sliding the apparatus over the color sample panel, and subsequently allowing the user to align the observation angle to a desired aspecular angle. In a preferred embodiment, the protractor has alignment angles for gloss (0) and the three DuPont metallic color control angles (15, 45, 110). One side of the protractor has a silver mirror tape and the other has a black glossy tape. The silver tape is for use with diffuse light sources such as a viewing booth. The black tape is for use with a spotlight such as the DuPont sunlight simulator. Looking at the reflected image of a spotlight in the silver tape would be uncomfortable.

Various modifications, alterations, additions, substitutions of the components of the apparatus of this invention will be apparent to those skilled in the art without departing from the spirit and scope of this invention. Since many embodiments may be made of this invention, it shall not be limited by the illustrative embodiments set forth herein, but rather is defined by the following claims.

What is claimed is:

1. An aspecular angular protractor apparatus useful for color evaluation, said protractor apparatus comprising:
  a) a cylindrical or semi-cylindrical shaped body,
  b) said body capable of securing a color sample upon the central axis of said body,
  c) said body having a glossy or mirrored reflective surface on the circumference, with one or more marks indicating specific aspecular viewing angles relative to the plane of said color sample, said angle being between the observation direction and the direction of specular reflection of a light source from the color sample surface.

2. The aspecular angular protractor of claim 1, wherein said body has marks upon the circumferential surface indicating 0°, 15°, 45°, and 110° aspecular viewing angles relative to the plane of said color sample, said angle being between the observation direction and the direction of specular reflection of a light source from the color sample surface.

3. The aspecular angular protractor of claim 1, wherein said mirrored reflective surface is positioned on the outer peripheral edge of the body.

4. The aspecular angular protractor of claim 1, wherein:
  a) said body is a hollow cylindrical shape,
  b) said body comprises a plurality of slots positioned on opposing peripheral surfaces of said body, said slots orientated to accept a planar shaped color sample upon the central axis of said body,
  c) said body having a glossy black and mirrored reflective surface strips on the circumferential surface, to ascertain the location of a light source reflection upon said surface, said body having marks upon the circumferential surface indicating 0°, 15°, 45°, and 110° aspecular viewing angles relative to the plane of said color sample, said angle being between the observation direction and the direction of specular reflection of a light source from the color sample surface.

5. A method of using an aspecular angular protractor apparatus for color evaluations, comprising the steps of:
  a) positioning and securing a color sample in the protractor apparatus of claim 1,
  b) aligning a visual light source with a target viewing angle as indicated on the circumference of said protractor,
  c) evaluating color at the specified viewing angle so that the visual observation is consistent with an instrumental color measurement at equal aspecular viewing angle.

6. The method of claim 5, wherein said viewing angles are taken at angles of about 15°, 45°, and 110° aspecular.

7. The aspecular angular protractor of claim 1, wherein said color sample to be evaluated is secured to said body.

8. The aspecular protractor of claim 7, wherein said color sample is a paint color sample which contains light reflecting metallic or pearl flakes.

9. The aspecular angular protractor of claim 1, wherein said protractor is a mobile device.

* * * * *